United States Patent
Carminati et al.

(10) Patent No.: US 7,700,613 B2
(45) Date of Patent: Apr. 20, 2010

(54) USE OF 7-T-BUTOXYIMINOMETHYLCAMPTOTHECIN FOR THE PREPARATION OF A MEDICAMENT FOR THE TREATMENT OF UTERINE NEOPLASMS

(75) Inventors: Paolo Carminati, Pomezia (IT); Marco Corsi, Pomezia (IT); Claudio Zanna, Pomezia (IT); Franco Cavalli, Bellinzona (CH); Luca Gianni, Milan (IT); Cristiana Sessa, Bellinzona (CH)

(73) Assignee: Sigma-Tau Farmaceutiche Riunite, S.p.A., Rome (IT)

( * ) Notice: Subject to any disclaimer, the term of this patent is extended or adjusted under 35 U.S.C. 154(b) by 0 days.

(21) Appl. No.: 11/628,458

(22) PCT Filed: Jun. 8, 2005

(86) PCT No.: PCT/IT2005/000320
§ 371 (c)(1),
(2), (4) Date: Aug. 1, 2007

(87) PCT Pub. No.: WO2005/120643
PCT Pub. Date: Dec. 22, 2005

(65) Prior Publication Data
US 2008/0020030 A1    Jan. 24, 2008

(30) Foreign Application Priority Data
Jun. 11, 2004   (IT) .................. RM2004A0288

(51) Int. Cl.
*A01N 43/42* (2006.01)
*A61K 31/44* (2006.01)
*C07D 491/00* (2006.01)

(52) U.S. Cl. .................. 514/283; 514/280; 546/48
(58) Field of Classification Search .................. None
See application file for complete search history.

(56) References Cited

U.S. PATENT DOCUMENTS 6,242,457 B1 * 6/2001 Penco et al. ............... 514/283
6,352,996 B1 * 3/2002 Cao et al. .................. 514/283
2004/0018988 A1 * 1/2004 Dallavalle et al. .......... 514/23
2007/0190128 A1 * 8/2007 Pisano et al. ............... 424/450

FOREIGN PATENT DOCUMENTS

| WO | 00/53607 | 9/2000 |
| WO | 03/043584 | 5/2003 |
| WO | 2004/103358 | 12/2004 |
| WO | WO 2004103358 A2 * | 12/2004 |

OTHER PUBLICATIONS

De Cesare et al. [Cancer Research 61, 7189-7195, Oct. 1, 2001].*
International Search Report for PCT/IT2005/000320 mailed Feb. 17, 2006.
Ulivi et al., *Cellular basis of antiproliferative and antitumor activity of the novel camptothecin derivative gimatecan, in bladder carcinoma models*, Neoplasia, 7(2), 152-161, 2005, XP008059631.
Cesare et al., *Potent Antitumor Activity and Improved Pharmacological Profile of ST1481, a Novel 7-substituted Camptothecin*, Cancer Research, vol. 61, 2001, pp. 7189-7195, XP002340217.
Kavanagh et al., *Irinotecan in cervical cancer*, Oncology, Aug. 1998, vol. 12, No. 8 Suppl 6, pp. 94-98, XP008059634.
Rothenberg, *CPT-11: an original spectrum of clinical activity*, Seminars in Oncology, Feb. 1996, vol. 23, No. 1 Suppl 3, pp. 21-26, XP008059635.
Fiorica, J.V., Update on the treatment of Cervical and Uterine Carcinoma: Focus on Topotecan, The Oncologist, 2002, 7(suppl 5):46-55.
Candelaria, et al., Radiosensitizers in cervical cancer. Cisplatin and beyond, Radiation Oncology 2006,1:15.
Chen, B. et al., "Elevated Topoisomerase I Activity in Cervical Cancer as a Target for Chemoradiation Therapy" Gynecologic Oncology, 79, 272-280 (2000) pp. 272-280.
Verschaegen, C. et al., "Topoisomerase-I Inhibitors in Gynaecologic Tumours" Annals of Academy of Medicine, vol. 27, No. 5, Sep. 1998, pp. 683-687.

* cited by examiner

*Primary Examiner*—Janet L. Epps-Smith
(74) *Attorney, Agent, or Firm*—Lucas & Mercanti, LLP

(57) ABSTRACT

The use of 7-ter-butoxyiminomethylcamptothecin is described in the preparation of a medicament useful for the treatment of uterine neoplasms, particularly cancer of the endometrium and of the neck of the womb.

5 Claims, No Drawings

USE OF 7-T-BUTOXYIMINOMETHYLCAMPTOTHECIN FOR THE PREPARATION OF A MEDICAMENT FOR THE TREATMENT OF UTERINE NEOPLASMS

This application is the US national phase of international application PCT/IT2005/000320 filed 8 Jun. 2005 which designated the U.S. and claims priority to IT RM2004A000288 filed 11 Jun. 2004, the entire contents of each of which are Hereby incorporated by reference.

The present invention relates to the use of 7-terbutoxyiminomethylcamptothecin for the preparation of a medicament with anticancer activity, particularly against uterine tumours.

BACKGROUND TO THE INVENTION

Anticancer chemotherapy agents are the drugs with the most restrictive therapeutic window. In fact, since their cytotoxic activity is non-selective, they can indiscriminately damage all the cells of the body with which they come into contact.

Over the past twenty years uterine cancers, the term including both cervical and endometrial carcinoma, have become the most frequent pelvic cancers in women. Surgery is the treatment of choice in most patients. The use of chemotherapy is generally confined to the treatment of metastatic or advanced disease. The chemotherapeutic agents commonly prescribed for the treatment of uterine cancers are characterised by a fairly low positive response level, ranging typically from 20% to 35%. There is therefore still a perceived need to identify an anticancer drug capable of yielding a higher positive response rate and at the same time presenting fewer side effects or at least to a more tolerable extent. 7-terbutoxyiminomethylcamptothecin (CPT184 or ST 1481 or gimatecan) is an orally active camptothecin derivative and is described in European Patent EP 1 044 977, where its activity on the non-small-cell lung cancer cell line is specified, and uterine cancers are not mentioned.

SUMMARY OF THE INVENTION

It has now been found that gimatecan is also active in uterine tumours, particularly of the endometrium and neck of the womb.

Therefore, one subject of the present invention is the use of 7-t-butoxyiminomethylcamptothecin, hereinafter also referred to as gimatecan, for the preparation of a medicament for the treatment of uterine cancers, particularly of the endometrium and neck of the womb.

Another object of the present invention is a method for treating a patient suffering from uterine neoplasm comprising administering to said patient an effective amount of 7-t-butoxyiminomethylcamptothe-cin.

The medicament which is the subject of the present invention will take the form of a pharmaceutical composition, such as is described, for example, in the above-mentioned European Patent. Preferably, the pharmaceutical form will be suitable for oral administration. In a preferred form, the active ingredient will be incorporated in liposomal formulations, such as are described, for example, in international patent application PCT/IT00/00137, or in some other form that allows its administration via the parenteral route.

The following example further illustrates the invention.

EXAMPLE 1

Gimatecan is a new anticancer compound that has shown a high therapeutic index in preclinical trials in vivo. Moreover, gimatecan is characterised by an anticancer activity that is maintained with different administration regimens, both intermittent and prolonged.

In the light of this preclinical evidence, a European phase I trial was conducted in which gimatecan was administered as a single therapeutic agent with different administration regimens. The patients studied were affected by advanced cancers for which curative or standard therapy was no longer indicated. Although the aim of the study was to assess the tolerability of the treatment with gimatecan, in the course of this clinical trial gimatecan produced a number of lasting objective clinical responses. Particularly worthy of mention are the responses of a number of patients with uterine cancers, both of the cervix and the endometrium, including forms which had received substantial previous treatments and presented metastatic disease. These clinical responses were defined as partial responses, that is to say they presented a more than 30% reduction of the tumour lesion or lesions, as assessed by means of diagnostic imagining techniques such as computed tomography.

These responses were subjected to two independent assessments by experts not taking part in the clinical trial, who confirmed the observations.

The invention claimed is:

1. A method for treating a patient suffering from advanced uterine neoplasm consisting of administering to said patient an effective amount of 7-t-butoxyiminomethylcamptothecin.

2. The method according to claim 1, wherein said neoplasm is cancer of the endometrium.

3. The method according to claim 1, wherein said neoplasm is cancer of the neck of the womb.

4. The method according to claim 1, wherein said 7-t-butoxyiminomethylcamptothecin is administered orally.

5. The method according to claim 1, wherein said 7-t-butoxyiminomethylcamptothecin is administered parenterally.

* * * * *